US011396488B2

(12) United States Patent
Brächer et al.

(10) Patent No.: US 11,396,488 B2
(45) Date of Patent: Jul. 26, 2022

(54) PROCESS FOR PREPARING ALDEHYDES AND SEPARATION OF THE CATALYST SYSTEM BY MEMBRANE SEPARATION

(71) Applicant: Evonik Operations GmbH, Essen (DE)

(72) Inventors: Alexander Brächer, Haltern am See (DE); Johannes Knossalla, Gahlen (DE); Dirk Fridag, Haltern am See (DE); Robert Franke, Marl (DE); Frederik Gluth, Mülheim an der Ruhr (DE); Marc Schäpertöns, Recklinghausen (DE); Christoph Kubis, Neinhagen (DE); Anna Chiara Sale, Recklinghausen (DE); Peter Kucmierczyk, Herne (DE); Ana Markovic, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/371,477

(22) Filed: Jul. 9, 2021

(65) Prior Publication Data
US 2022/0033337 A1 Feb. 3, 2022

(30) Foreign Application Priority Data

Jul. 30, 2020 (EP) .................... 20188523

(51) Int. Cl.
*C07C 45/50* (2006.01)
*B01D 71/00* (2006.01)
*C07C 45/78* (2006.01)
*B01D 71/52* (2006.01)
*B01D 71/70* (2006.01)
*B01J 31/18* (2006.01)

(52) U.S. Cl.
CPC ............ *C07C 45/786* (2013.01); *B01D 71/52* (2013.01); *B01D 71/70* (2013.01); *B01J 31/185* (2013.01); *C07C 45/505* (2013.01); *B01J 2231/321* (2013.01); *B01J 2531/822* (2013.01)

(58) Field of Classification Search
CPC ..... C07C 45/50; C07C 45/505; C07C 45/786; B01D 71/52
See application file for complete search history.

(56) References Cited

U.S. PATENT DOCUMENTS

| | | | |
|---|---|---|---|
| 8,226,829 B2 | 7/2012 | Wiese et al. | |
| 8,969,628 B2 | 3/2015 | Priske et al. | |
| 10,501,392 B2 | 12/2019 | Fridag et al. | |
| 10,633,302 B2 | 4/2020 | Nadolny et al. | |
| 10,647,650 B2 | 5/2020 | Hecht et al. | |
| 10,654,784 B2 | 5/2020 | Hasselberg et al. | |
| 10,850,261 B2 | 12/2020 | Nadolny et al. | |
| 10,882,027 B2 | 1/2021 | Nadolny et al. | |
| 11,008,275 B2 | 5/2021 | Kucmierczyk et al. | |
| 2019/0283004 A1 | 9/2019 | Nadolny et al. | |
| 2020/0391194 A1 | 12/2020 | Kucmierczyk et al. | |
| 2020/0392057 A1 | 12/2020 | Kucmierczyk et al. | |
| 2020/0392064 A1 | 12/2020 | Kucmierczyk et al. | |
| 2021/0179534 A1 | 6/2021 | Schulz et al. | |

FOREIGN PATENT DOCUMENTS

| | | | |
|---|---|---|---|
| WO | 2007/036424 A1 | 4/2007 | |
| WO | 2010/097376 A1 | 9/2010 | |

OTHER PUBLICATIONS

European Search Report dated Nov. 29, 2021 in EP 21184642.3 (7 pages).

*Primary Examiner* — Sikarl A Witherspoon
(74) *Attorney, Agent, or Firm* — Taylor English Duma LLP; Philip P. McCann

(57) ABSTRACT

The present invention provides a process for preparing aldehydes from C2 to C20 olefins using a subsequent membrane separation to separate the homogeneously dissolved catalyst system, wherein prior to the membrane separation a gas exchange that increases the partial pressure fraction of carbon monoxide or hydrogen is carried out in order to boost catalyst retention by the membrane.

21 Claims, No Drawings

PROCESS FOR PREPARING ALDEHYDES AND SEPARATION OF THE CATALYST SYSTEM BY MEMBRANE SEPARATION

CROSS REFERENCE TO RELATED APPLICATIONS

This application is a 35 U.S.C. § 119 patent application which claims the benefit of European Application No. 20188523.3 filed Jul. 30, 2020, which is incorporated herein by reference in its entirety.

FIELD

The present invention relates to a process for preparing aldehydes from C2 to C20 olefins using a subsequent membrane separation to separate the homogeneously dissolved catalyst system, wherein prior to the membrane separation a gas exchange that increases the partial pressure fraction of carbon monoxide or hydrogen is carried out in order to boost catalyst retention by the membrane.

BACKGROUND

Hydroformylation processes for preparing aldehydes have long been known to those skilled in the art. In these processes, olefins are converted into the corresponding aldehydes by reaction with syngas, a mixture of carbon monoxide (CO) and hydrogen ($H_2$), in the presence of a catalyst system. Hydroformylation is a process employed in industry in plants capable of producing hundreds of kilotonnes (kt) of aldehyde per year. The catalyst systems typically used here are homogeneously dissolved catalyst systems and comprise transition metal complexes of mostly cobalt or rhodium as the metal and phosphorus-containing ligands.

The ability to economically operate such hydroformylation processes on a scale of hundreds of kt depends on various factors. One important factor is the metal in the homogeneously dissolved catalyst system, since rhodium and cobalt and compounds thereof employed as catalyst precursor are relatively costly raw materials. A core objective in the operation of industrial hydroformylation processes is accordingly the minimization of catalyst losses during operation. One known measure is the separation of the homogeneously dissolved catalyst system from the reaction output and recycling the catalyst system into the reaction zone. This can be done for example by means of known membrane separation processes (see e.g. WO 2010/097376 A1). The known membrane separation processes are executed here such that either the reaction output pressurized with syngas is supplied to the membrane separation or the reaction output is first subjected to a thermal separation (distillation, evaporation in a thin-film evaporator (TFE)), wherein the reaction output must first be depressurized and the membrane separation then performed thereafter, optionally under pressurization with an inert gas such as nitrogen.

Catalyst losses can however additionally occur during or before the known separation processes, whether through adhesion of clusters in parts of the system, caused by precipitation of insoluble transition metal compounds in the system, or through inadequate separation of the catalyst system from the reactor output.

SUMMARY

The object of the present invention was accordingly to provide a process for preparing aldehydes in which the catalyst losses during separation of the homogeneously dissolved catalyst system by membrane separation are decreased compared to known processes.

DETAILED DESCRIPTION

It has surprisingly been found that this object can be achieved by carrying out a gas exchange after the actual reaction, but before the membrane separation. In this process, the syngas, that is to say a mixture comprising mainly carbon monoxide and hydrogen, is at least partially replaced by carbon monoxide or hydrogen, as a result of which the partial pressure fraction of carbon monoxide or hydrogen is increased. The product-containing reaction output or output from a thermal separation arranged upstream of the membrane separation is thus pressurized with a gas having a composition different to that in the reaction, or with a gas mixture having a different blend, which in the subsequent membrane separation, results in increased retention and hence better separation of the homogeneously dissolved catalyst system.

The invention consequently achieves the object through a process for preparing aldehydes, said process comprising at least a hydroformylation through the reaction of C2 to C20 olefins, preferably C2 to C17 olefins, more preferably C3 to C14 olefins and most preferably C6 to C14 olefins, with syngas in the presence of a homogeneously dissolved catalyst system that comprises at least Co or Rh and preferably a phosphorus-containing ligand, in at least one reaction zone, yielding a liquid reaction output containing the product, wherein the partial pressure fraction of CO or $H_2$ in the hydroformylation constitutes not more than 75% of the total gas pressure, preferably not more than 70% of the total gas pressure, more preferably not more than 65% of the total gas pressure, the total gas pressure being the sum of the pressures occurring from all the gaseous substances present, and a membrane separation for separating the homogeneously dissolved catalyst system, characterized in that, before the membrane separation, a gas exchange with CO or $H_2$ is carried out, as a result of which the partial pressure fraction of CO or $H_2$ constitutes more than 80% of the total gas pressure, preferably more than 85% of the total gas pressure, more preferably more than 90% of the total gas pressure.

The first part of the process of the invention is the hydroformylation of C2-C20 olefins, preferably C2 to C17 olefins, more preferably C3 to C14 olefins and most preferably C6 to C14 olefins. In principle, the pure olefins may be used in the process. Preference is however given to using hydrocarbon streams comprising the appropriate olefins. The olefin content of the hydrocarbon streams should naturally be sufficiently high for it to be possible to operate a hydroformylation economically. The olefin-containing feedstock mixtures preferably contain practically no further unsaturated compounds or polyunsaturated compounds such as dienes or acetylene derivatives.

The hydrocarbon streams that can be used in the process of the invention may comprise olefins having terminal and/or internal carbon-carbon double bonds. In addition, the recited hydrocarbon streams may comprise olefins having the same number or different numbers of carbon atoms. Suitable olefins are in particular ethene, propene, 1- or 2-butene or mixtures thereof, isobutene, 1- or 2-pentene or mixtures thereof, isopentene, 1-, 2- or 3-hexene, 1-heptene, linear heptenes having an internal double bond (2-heptene, 3-heptene, etc.), mixtures of linear heptenes, 2- or 3-methyl-1-hexene, 1-octene, linear octenes having an internal double bond, mixtures of linear octenes, 2- or 3-methylheptene, 1-nonene, linear nonenes having an internal double bond, mixtures of linear nonenes, 2-, 3- or 4-methyloctene, 1-, 2-, 3-, 4- or 5-decene, 2-ethyl-1-octene, 1-dodecene, linear dodecenes having an internal double bond, mixtures of linear dodecenes, 1-tetradecene, linear tetradecenes having an internal double bond, mixtures of linear tetradecenes, 1-hexadecene, linear hexadecenes having an internal double bond and mixtures of linear hexadecenes.

Propylene is produced industrially by the cracking of naphtha and is a basic chemical that is readily available. C5 olefins, that is to say pentenes, are present in light petroleum fractions from refineries or crackers. Technical mixtures comprising linear C4 olefins, n-butene and isobutene are light petroleum fractions from refineries, C4 fractions from FC crackers or steam crackers, mixtures from Fischer-Tropsch syntheses, mixtures from the dehydrogenation of butanes, and mixtures resulting from metathesis or other industrial processes. For example, mixtures of linear butenes suitable for the process of the invention are obtainable from the C4 fraction of a steam cracker.

The higher olefins can in particular be obtained by oligomerization reactions, for example dimerization, trimerization or tetramerization. Suitable hydrocarbon streams are in addition the mixture of isomeric hexenes (dipropene) resulting from the dimerization of propene, the mixture of isomeric octenes (dibutene) resulting from the dimerization of butenes, the mixture of isomeric nonenes (tripropene) resulting from the trimerization of propene, the mixture of isomeric dodecenes (tetrapropene or tributene) resulting from the tetramerization of propene or the trimerization of butenes, the isomeric hexadecenes (tetrabutene) resulting from the tetramerization of butenes and also the olefin mixtures produced by the co-oligomerization of olefins having a varying number of carbon atoms (preferably 2 to 4 carbon atoms), optionally after distillative separation into fractions having the same or different numbers of carbon atoms. Olefins or olefin mixtures produced by Fischer-Tropsch synthesis may also be used. It is additionally possible to use olefins produced by olefin metathesis or by other industrial processes.

The olefins used in the process are hydroformylated with syngas in the presence of a homogeneously dissolved catalyst system. The molar ratio between syngas and the feedstock mixture should be between 6:1 and 1:1, preferably between 3:1 and 1:1, more preferably between 2:1 and 1:1. The hydroformylation may optionally be carried out in the presence of a solvent known to those skilled in the art, but it is preferable to use no solvent.

The homogeneous catalyst system used in the process of the invention comprises or consists of Co or Rh, preferably Rh, and preferably a phosphorus-containing ligand. In a particularly preferred embodiment, the catalyst system of the invention comprises or consists of Rh and a phosphorus-containing ligand. Suitable ligands for the catalyst systems of the invention are known to those skilled in the art (see e.g. the textbooks "Rhodium Catalyzed Hydroformylation" (from 2002) by P.W.N.M. van Leeuwen or "Hydroformylation—Fundamentals, Processes and Applications in Organic Synthesis" (from 2016) by A. Borner and R. Franke).

The phosphorus-containing ligand for the catalyst system of the invention is preferably a phosphine (e.g. TPP (triphenylphosphine)), a monophosphite (e.g. Alkanox 240 (tris (2,4-di-tert-butylphenyl)phosphite)) or a bisphosphite (e.g. BiPhePhos). It is also possible to use mixtures of ligands.

The hydroformylation is preferably carried out under the following conditions: The temperature in the hydroformylation is preferably within a range from 80 to 250° C., more preferably within a range from 90 to 225° C. and particularly preferably within a range from 100 to 210° C. The pressure in the hydroformylation is preferably within a range from 10 to 350 bar, more preferably within a range from 30 to 325 bar and particularly preferably within a range from 45 to 300 bar.

The hydroformylation is according to the invention carried out in at least one reaction zone. A reaction zone for the purposes of the present invention comprises at least one reactor in which the hydroformylation is carried out. It is also possible for the reaction zone to comprise more than one reactor, in particular two or three reactors, which can be connected in parallel or in series or arranged in a hybrid of parallel and serial connection.

The pressure in the hydroformylation normally corresponds to the total gas pressure. The total gas pressure in the context of the present invention means the sum of the pressures occurring from all the gaseous substances present, that is to say the pressure of the (total) gas phase. In the present invention, this corresponds in particular to the sum of the partial pressures of $H_2$, i.e. the total gas pressure is then the syngas pressure. In the hydroformylation of the invention, the partial pressure fraction of either CO or $H_2$ constitutes not more than 70% of the total gas pressure, preferably not more than 60% of the total gas pressure, more preferably not more than 55% of the total gas pressure.

The liquid reaction output containing the product and obtained in the hydroformylation is accordingly also under the pressure present during the hydroformylation. The hydroformylation is then followed by the performance of a thermal separation or a membrane separation. A thermal separation is however optional here, that is to say it does not need to be carried out, whereas the process of the invention always includes a membrane separation. It is also possible for the thermal separation to be carried out only once the membrane separation has been performed. In a specific case it is possible for a membrane separation to be carried out both before and after the thermal separation.

The thermal separation, when an optional step of this kind is being carried out, can thus be carried out before or after the membrane separation. The thermal separation may consist of a single process step or more than one. The thermal separation comprises at least one thermal separation process preferably selected from thin-film evaporation, distillation, falling-film evaporation and short-path evaporation.

In a preferred embodiment of the present invention, the thermal separation takes place before the membrane separation, but the gas exchange according to the invention takes place after the thermal separation and before the membrane separation.

The membrane separation carried out after the hydroformylation, optionally preceded or followed by a thermal separation as described above, is carried out in order to separate the homogeneously dissolved catalyst system.

Before the membrane separation, optionally before a thermal separation upstream of the membrane separation, a gas exchange with CO or $H_2$ is carried out, as a result of which the partial pressure fraction of CO or $H_2$ thereafter constitutes more than 80% of the total gas pressure, preferably more than 85% of the total gas pressure, more preferably more than 90% of the total gas pressure. The partial pressure fraction of either CO or $H_2$ is selectively increased by this gas exchange, while the partial pressure fraction of the respective other components is decreased. Possible processes for the gas exchange are known to those skilled in the art.

The liquid reaction output containing the product is, as mentioned, still under pressure after the hydroformylation as a result of the syngas present. If a thermal separation takes place before the membrane separation, it is also possible for a different or an additional gas to be present, for example an inert gas. The gas exchange before the membrane separation takes place for example by at least partially discharging the gas present, i.e. depressurizing the reaction output or the output from the thermal separation, and then pressurizing with CO or $H_2$ until the desired partial pressure fraction of CO or $H_2$, that is to say more than 80% of the total gas pressure, preferably more than 85% of the total gas pressure, more preferably more than 90% of the total gas pressure, is present. In another variant, the depressurization of the output from the reaction or from the thermal separation is followed by pressurization with CO or $H_2$ using a mixing zone and/or a bubble column until the desired partial pressure fraction of CO or $H_2$, that is to say more than 80% of the total gas pressure, preferably more than 85% of the total gas pressure, more preferably more than 90% of the total gas pressure, is present.

The discharge of the gas/depressurization of the liquid reaction output or the output from the thermal separation and the subsequent pressurization with CO or $H_2$, optionally using a mixing zone and/or a bubble column, can be carried out once or two or more times in succession in order to set the desired partial pressure fraction. After the gas exchange, the total gas pressure is preferably 1 to 70 bar, more preferably 2 to 30 bar and particularly preferably 4 to 20 bar.

After the gas exchange, the liquid reaction output or the output from an upstream thermal separation is subjected to the membrane separation in order to separate the homogeneous catalyst system. The membrane separation is preferably carried out at a transmembrane pressure of 5 to 100 bar, more preferably 10 to 80 bar and particularly preferably 20 to 50 bar. In a preferred embodiment, the membrane separation is in addition carried out at a temperature of 0° C. to 200° C., more preferably between 20° C. and 160° C.

The membrane material used in the membrane separation is preferably selected from the group consisting of polydimethylsiloxanes, polyimides, partially fluorinated polymers, completely fluorinated polymers, perfluorinated polymers, amorphous fluoropolymers (e.g. Cytop®), amorphous or partially crystalline perfluoroalkoxy polymers (e.g. Hyflon®), block copolymers of the abovementioned materials, polymers having intrinsic microporosity (PIM), polyaryletherketones, in particular polyetheretherketones and polyetherketoneketones, polybenzimidazoles and polyethers. Also suitable are polymers having intrinsic microporosity (PIMs) of diverse monomer composition, in particular those containing spirobifluorene groups. The membrane material is preferably a polydimethylsiloxane (PDMS) or a perfluoroalkoxy polymer such as Hyflon®.

In a preferred embodiment, the membrane material used is intrinsically stable in the reaction output/in the mixture present after the thermal separation, i.e. it does not require any additional crosslinking of the polymer chains.

The process of the invention may be carried out continuously or batchwise. In a preferred embodiment, the process is carried out continuously.

The present invention is elucidated hereinbelow with reference to examples. These examples do not however constitute any restriction, but serve only for illustration.

EXAMPLES

Example 1—Gas Exchange with Hydrogen and Carbon Monoxide in Toluene

Experimental Setup

Dicarbonyl(acetylacetonato)rhodium(I) (1.97 g, 7.63 mmol) as precursor for the transition metal of the catalyst system and the phosphorus-containing ligand Alkanox® 240 (tris(2,4-di-tert-butylphenyl)phosphite)) (98.74 g, 152.6 mmol) were dissolved in toluene (2612.1 g) in a rhodium: ligand molar ratio of 1:20 at an Rh concentration of 300 ppm by mass.

This solution was subjected to a membrane separation in a membrane test apparatus with closed circulation in which the permeate and excess retentate are recycled back into the feed. This continuous circulation mode ensures that the separation conditions for the membrane, such as the feed concentration and viscosity, remain similar over the duration of the experiment. The tested membrane having a membrane area of 84.5 $cm^2$ was sealed in a flat-channel test cell. The membrane material used was crosslinked polydimethylsiloxane (PDMS).

The catalyst was first preformed at a syngas pressure of 40 bar at 60° C. in the reactor without membrane separation. The reactor was then depressurized to a total gas pressure of 20 bar, the temperature lowered to 30° C. and then the flat-channel test cells put into operation. The membrane circulation was operated at 30° C. and at a feed pressure of 50 bar and a permeate pressure of 21 bar.

Measurement of Retention

The first measurement, measurement 1, was carried out at a reactor pressure of 20 bar syngas (CO:$H_2$ mixture=approx. 50:50). Samples were collected in each case of the feed, retentate and permeate and the rhodium concentration thereof was investigated by ICP-MS in order to determine therefrom the rhodium retention (rhodium retention=1−(Rh concentration in the permeate/Rh concentration in the retentate). The rhodium retention was 73%.

With the membrane separation running, a gas exchange was subsequently carried out in which the reactor was several times depressurized to 2 bar and then repressurized with hydrogen to 20 bar. This pressure exchange consisting of depressurization and repressurization with hydrogen was repeated three times. The partial pressure fraction of hydrogen thereafter constituted more than 90% of the total gas pressure. Measurement 2 was then carried out with this feed. Samples were collected of both the feed and the permeate and the rhodium concentration thereof investigated in order to determine therefrom the rhodium retention. The rhodium retention after pressurization with hydrogen was 80%. This demonstrates that it was possible to markedly increase the retention of rhodium in the membrane separation by prior pressurization with hydrogen instead of syngas.

This was followed, similarly to the gas exchange from syngas to hydrogen, by the reverse gas exchange returning from hydrogen to syngas pressure, in order to restore the starting situation (measurement 3). The rhodium retention thereafter was 70%.

A further gas exchange was thereafter carried out in a similar manner, but this time carrying out a gas exchange to carbon monoxide (measurement 4). The rhodium retention thereafter was 78%. This demonstrates that it was also possible to markedly increase the retention of rhodium in the membrane separation by prior pressurization with carbon monoxide instead of syngas.

The results are summarized again in the table below:

| Measurement | Retention of rhodium by the membrane |
|---|---|
| 1 (syngas) | 73% |
| 2 (hydrogen) | 80% |
| 3 (syngas) | 70% |
| 4 (carbon monoxide) | 78% |

Example 2—Gas Exchange with Hydrogen and Carbon Monoxide in Isotridecanal

The experiment described in example 1 was repeated with isotridecanal instead of toluene. For this, dicarbonyl(acetylacetonato)rhodium(I) (1.174 g, 4.55 mmol) and Alkanox® 240 (tris(2,4-di-tert-butylphenyl)phosphite) (58.31 g, 152.6 mmol) were dissolved in isotridecanal (2492.02 g) in a rhodium:ligand molar ratio of 1:20 at an Rh concentration of 300 ppm by mass. The experimental setup and the procedure were carried out as described in example 1.

Here too it was found that, both after pressurization with hydrogen and after pressurization with carbon monoxide, the membrane retention was higher than in the comparison interval with syngas.

The results with isotridecanal as solvent are summarized in the table below:

| Measurement | Retention of rhodium by the membrane |
|---|---|
| 1 (syngas) | 30% |
| 2 (hydrogen) | 45% |
| 3 (syngas) | 21% |
| 4 (carbon monoxide) | 40% |

Example 3—Gas Exchange with Hydrogen and Carbon Monoxide in Toluene with Membrane Made of Polyetheretherketone The experiment described in example 1 was repeated with toluene and with a membrane made of polyetheretherketone (PEEK) instead of a membrane made of crosslinked PDMS. The membrane made of PEEK was produced according to WO 2015/110843 A1 (example 1). Dicarbonyl(acetylacetonato)rhodium(I) (1.824 g, 7.07 mmol) and Alkanox® 240 (tris(2,4-di-tert-butylphenyl)phosphite)) (90.85 g, 140.4 mmol) were dissolved in toluene (2431 g) in a rhodium:ligand molar ratio of 1:20 at an Rh concentration of 300 ppm by mass. The experimental setup and the procedure were carried out as described in example 1.

Here too it was found that, both after pressurization with hydrogen and after pressurization with carbon monoxide, the membrane retention was higher than in the comparison interval with syngas.

The results with toluene as solvent and a membrane made of PEEK are summarized in the table below:

| Measurement | Retention of rhodium by the membrane |
|---|---|
| 1 (syngas) | 89% |
| 2 (hydrogen) | 96% |
| 3 (syngas) | 90% |
| 4 (carbon monoxide) | 95% |

Example 4—Gas Exchange with Hydrogen and Carbon Monoxide in Toluene with SolSep NF030306

The experiment described in example 1 was repeated with a commercially available membrane, NF030306 from SolSep BV.

Dicarbonyl(acetylacetonato)rhodium(I) (1.825 g, 7.07 mmol) and Alkanox® 240 (tris(2,4-di-tert-butylphenyl) phosphite)) (90.90 g, 140.5 mmol) were dissolved in toluene (2448 g) in a rhodium:ligand molar ratio of 1:20 at an Rh concentration of 300 ppm by mass. The experimental setup and the procedure were carried out as described in example 1.

Here too it was found that, both after pressurization with hydrogen and after pressurization with carbon monoxide, the membrane retention was higher than in the comparison interval with syngas.

The results with toluene as solvent and the membrane SolSep NF030306 are summarized in the table below:

| Measurement | Retention of rhodium by the membrane |
|---|---|
| 1 (syngas) | 63% |
| 2 (hydrogen) | 74% |
| 3 (syngas) | 66% |
| 4 (carbon monoxide) | 71% |

The invention claimed is:

1. A process for preparing aldehydes, said process comprising the steps of
   a hydroformylation through reacting of C2 to C20 olefins with syngas in the presence of a homogeneously dissolved catalyst system that comprises at least Co or Rh, in at least one reaction zone, yielding a liquid reaction output containing the product, wherein the partial pressure fraction of CO or $H_2$ in the hydroformylation constitutes not more than 75% of the total gas pressure, the total gas pressure being the sum of the pressures occurring from all the gaseous substances present, and the process has a molar ratio of syngas and feedstock mixture comprising the C2 to C20 olefins and the homogeneously dissolved catalyst system of between 6:1 and 1:1, and separating the homogeneously dissolved catalyst system with a membrane separation, wherein, before the membrane separation, carrying out a gas exchange with CO or $H_2$, as a result of which the partial pressure fraction of CO or $H_2$ constitutes more than 80% of the total gas pressure.

2. The process according to claim 1, wherein the hydroformylation is carried out at a pressure of from 10 to 350 bar, and a molar ratio of syngas and the feedstock mixture of between 3:1 and 1:1.

3. The process according to claim 1, wherein the hydroformylation is carried out at a temperature of from 80 to 250° C., and a molar ratio of syngas and the feedstock mixture of between 2:1 and 1:1.

4. The process according to claim 1, wherein the homogeneously dissolved catalyst system comprises at least Rh and a phosphorus-containing ligand.

5. The process according to claim 1, wherein the phosphorus-containing ligand is a phosphine, a monophosphite, a bisphosphite or mixtures thereof.

6. The process according to claim 1, wherein the total gas pressure after the gas exchange is from 1 to 70 bar.

7. The process according to claim 1, wherein the membrane separation is carried out at a transmembrane pressure of from 5 to 100 bar.

8. The process according to any of claim 1, wherein the membrane separation is carried out at a temperature of from 0° C. to 200° C.

9. The process according to claim 1, wherein at least one thermal separation is carried out before or after the membrane separation.

10. The process according to claim 9, wherein the thermal separation comprises at least one thermal separation process selected from the group consisting of thin-film evaporation, distillation, falling-film evaporation and short-path evaporation.

11. The process according to claim 9, wherein the thermal separation takes place before the membrane separation, but the gas exchange takes place after the thermal separation and before the membrane separation.

12. The process according to claim 1, wherein the process is carried out continuously.

13. The process according to claim 1, wherein the reaction zone comprises at least one reactor.

14. The process according to claim 1, wherein the membrane separation uses a membrane material selected from the group consisting of polydimethylsiloxanes, polyimides, partially fluorinated polymers, completely fluorinated polymers, perfluorinated polymers, amorphous fluoropolymers, amorphous or partially crystalline perfluoroalkoxy polymers, block copolymers of the abovementioned materials, polymers having intrinsic microporosity (PIM), polyetheretherketones, polyetherketoneketones, polybenzimidazoles and polyethers.

15. The process according to claim 14, wherein a membrane material is used that is intrinsically stable in the reaction output/in the mixture present after the thermal separation, i.e. it does not require any additional crosslinking of the polymer chains.

16. The process according to claim 1, wherein
a hydroformylation through the reaction of C2 to C17 olefins with syngas in the presence of a homogeneously dissolved catalyst system that comprises at least Co or Rh and a phosphorus-containing ligand, in at least one reaction zone, yielding a liquid reaction output containing the product, wherein the partial pressure fraction of CO or $H_2$ in the hydroformylation constitutes not more than 70% of the total gas pressure, the total gas pressure being the sum of the pressures occurring from all the gaseous substances present, and a molar ratio of syngas and the feedstock mixture of between 3:1 and 1:1, and
a membrane separation for separating the homogeneously dissolved catalyst system, wherein,
before the membrane separation, a gas exchange with CO or $H_2$ is carried out, as a result of which the partial pressure fraction of CO or $H_2$ constitutes more than 85% of the total gas pressure.

17. The process according to claim 1, wherein
a hydroformylation through the reaction of C3 to C14 olefins with syngas in the presence of a homogeneously dissolved catalyst system that comprises at least Co or Rh and a phosphorus-containing ligand, in at least one reaction zone, yielding a liquid reaction output containing the product, wherein the partial pressure fraction of CO or $H_2$ in the hydroformylation constitutes not more than 70% of the total gas pressure, the total gas pressure being the sum of the pressures occurring from all the gaseous substances present, and a molar ratio of syngas and the feedstock mixture of between 2:1 and 1:1, and
a membrane separation for separating the homogeneously dissolved catalyst system, wherein,
before the membrane separation, a gas exchange with CO or $H_2$ is carried out, as a result of which the partial pressure fraction of CO or $H_2$ constitutes more than 85% of the total gas pressure.

18. The process according to claim 1, wherein
a hydroformylation through the reaction of C6 to C14 olefins with syngas in the presence of a homogeneously dissolved catalyst system that comprises at least Co or Rh and a phosphorus-containing ligand, in at least one reaction zone, yielding a liquid reaction output containing the product, wherein the partial pressure fraction of CO or $H_2$ in the hydroformylation constitutes not more than 65% of the total gas pressure the total gas pressure being the sum of the pressures occurring from all the gaseous substances present, and a molar ratio of syngas and the feedstock mixture of between 3:1 and 1:1, and
a membrane separation for separating the homogeneously dissolved catalyst system, wherein,
before the membrane separation, a gas exchange with CO or $H_2$ is carried out, as a result of which the partial pressure fraction of CO or $H_2$ constitutes more than 90% of the total gas pressure.

19. The process according to claim 1, wherein the total gas pressure after the gas exchange is from 4 to 20 bar.

20. The process according to claim 1, wherein the membrane separation is carried out at a transmembrane pressure of from 20 to 50 bar.

21. The process according to claim 1, wherein the membrane separation is carried out at a temperature of from 20° C. to 160° C.

* * * * *